United States Patent [19]
Lavielle et al.

[11] Patent Number: 4,812,469
[45] Date of Patent: Mar. 14, 1989

[54] ACETAMIDES DERIVED FROM 2,3-DIHYDRO-3-PHENYL-2-BENZOFURANONE

[75] Inventors: Gilbert Lavielle, LaCelle Saint-Cloud; Jean Lepagnol, Chatou, both of France

[73] Assignee: Adir Et Cie, Neuilly-sur-Seine, France

[21] Appl. No.: 155,353

[22] Filed: Feb. 12, 1988

[30] Foreign Application Priority Data

Feb. 27, 1987 [FR] France .................. 87 02631

[51] Int. Cl.$^4$ ............... A61K 31/34; C07D 307/78
[52] U.S. Cl. ................. 514/466; 549/304; 514/470; 514/253; 514/233.5; 544/364; 544/377; 544/376; 544/153
[58] Field of Search ........... 549/304; 514/466, 470

[56] References Cited

U.S. PATENT DOCUMENTS 2,472,666  6/1949  Leekley ................. 549/304

FOREIGN PATENT DOCUMENTS 0176309  4/1986  United Kingdom .......... 549/304

OTHER PUBLICATIONS

Chemical Abstracts, vol. 93 (1980), p. 108.
Shridhar, D. R., et al., "Benzofuran Derivatives: Part III", Indian Journal of Chemistry, vol. 19B, Oct. 1980, pp. 891–893.

Primary Examiner—Mary C. Lee
Assistant Examiner—Robert C. Whittenbaugh
Attorney, Agent, or Firm—Gordon W. Hueschen

[57] ABSTRACT

The invention relates to new acetamides derived from 2,3-dihydro-3-phenyl-2-benzofuranone, of general formula I

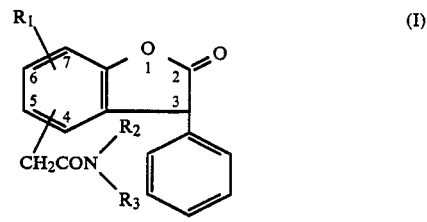

in which:
$R_1$ denotes a hydrogen or halogen atom,
$R_2$ and $R_3$, which may be identical or different, each denote a hydrogen atom or a linear or branched alkyl radical containing 1 to 4 carbon atoms, a benzyl radical optionally substituted with a halogen atom, with an alkoxy radical containing 1 to 4 carbon atoms or with an alkyl radical having 1 to 4 carbon atoms, or a 3,4-methylenedioxybenzyl radical, or form, together with the nitrogen to which they are attached, a 4-morpholinyl radical or a 1-piperazinyl radical.

9 Claims, No Drawings

ACETAMIDES DERIVED FROM 2,3-DIHYDRO-3-PHENYL-2-BENZOFURANONE

The present invention relates to new 2,3-dihydro-3-phenyl-2-benzofuranone derivatives, processes for preparing them and pharmaceutical compositions which contain them.

Surprisingly, few pharmacologically active 2,3-dihydro-2-benzofuranone compounds are mentioned in the literature. A few esters of 2-(2,3-dihydro-2-oxo-3-phenyl-5-benzofuranyl)acetic acid having antiinflammatory properties have been described by Shridhar et al. in Indian J. Chem. (1980), vol. 19B (10), p. 891–893.

The Applicant has now discovered that certain acetamides derived from 2,3-dihydro-3-phenyl-2-benzofuranone possess very advantageous pharmacological properties.

In effect, the compounds of the present invention exert antihypoxic and nootropic effects without producing vascular effects. They significantly counteract brain death and tissue energy lack in the case of insufficiency of the oxygen supply, and find their application in the correction of disorders linked to hypoxemia and energy insufficiency, for example during cerebral aging.

The subject of the present invention is more especially the compounds of general formula I

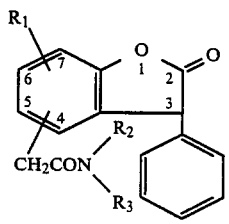
(I)

in which:
either $R_1$ is at the 7-position and the acetamido group is at the 5-position, or $R_1$ is at the 5-position and the acetamido group is at the 7-position, $R_1$ denotes a hydrogen or halogen atom, $R_2$ and $R_3$, which may be identical or different, each denote a hydrogen atom or a linear or branched alkyl radical containing 1 to 4 carbon atoms, a benzyl radical optionally substituted with a halogen atom, with an alkoxy radical containing 1 to 4 carbon atoms or with an alkyl radical having 1 to 4 carbon atoms, or a 3,4-methylenedioxybenzyl radical, or form, together with the nitrogen to which they are attached, a 4-morpholinyl radical or a 1-piperazinyl radical (optionally substituted at the 4-position with an alkyl radical having 1 to 4 carbon atoms, a benzyl radical optionally substituted with an alkyl radical having 1 to 4 carbon atoms, a 3,4-methylenedioxybenzyl radical, or a 2-pyridyl radical optionally substituted with an alkyl radical having 1 to 4 carbon atoms or a trifluoromethyl radical), and their addition salts with a pharmaceutically acceptable inorganic or organic acid.

The subject of the present invention is also the process for preparing the compounds of general formula I, wherein mandelic acid is condensed with a hydroxyphenylacetic acid compound of general formula II

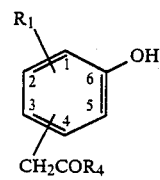
(II)

in which $R_1$ has the same meaning defined above for the formula I, $R_4$ denotes a hydroxyl radical or an amino radical of formula III

(III)

in which $R_2$ and $R_3$ have the meaning defined above for the formula I, and either $R_1$ is in the 1-position and the radical —$CH_2COR$ is in the 3-position, or $R_1$ is in the 3-position and the radical —$CH_2COR_4$ is in the 1-position, to form either the compounds of general formula I when $R_4$ is an amino radical of formula III, or an acid of general formula IV

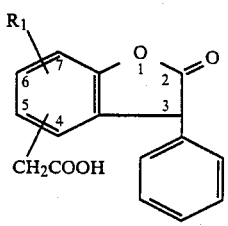
(IV)

in which the meaning of $R_1$ remains identical to that given above, and either $R_1$ is at the 7-position and the carboxymethylene radical at the 5-position, or $R_1$ is at the 5-position and the carboxymethylene radical at the 7-position, which is then subjected to the action of thionyl chloride to form a compound of general formula V

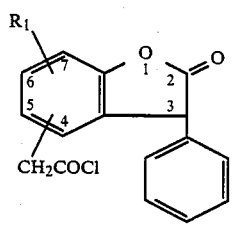
(V)

in which the meaning of $R_1$ remains identical to that given above, and either $R_1$ is at the 7-position and the chloroformylmethylene radical at the 5-position, or $R_1$ is at the 5-position and the chloroformylmethylene radical at the 7-position, which is condensed with an amine of general formula VI

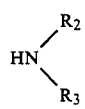

in which $R_2$ and $R_3$ have the meaning defined above for the formula I, to obtain the compounds of general formula I, which can then, if desired, be salified with a pharmaceutically acceptable inorganic or organic acid.

When they are derivatives of 2-hydroxyphenylacetamide, compounds of general formual II are prepared according to traditional processes [Bericht. (1895) 28, p. 989], and when they are derivatives of 4-hydroxyphenylacetamide, according to the processes described in Chem. Abst. 50, 4990i or in J. Am. Chem. Soc. (1946) p. 2633.

The condensation of mandelic acid with the compounds of general formula II is performed in acid medium and at a temperature between 50° C. and 120° C.

The acyl halides of general formula V are prepared at a temperature between 50° C. and 100° C. in an apolar anhydrous organic solvent, by reacting thionyl chloride with the acids of general formula IV.

The condensation of the amines of general formula VI with the compounds of general formula V is performed in alkaline medium in an anhydrous apolar organic solvent and at room temperature.

Among the pharmaceutically acceptable acids for preparing the addition salts with the compounds of general formula I, hydrochloric, phosphoric, citric, oxalic, sulfuric, tartaric, maleic, mandelic and methanesulfonic acids, and the like, may be mentioned.

The compounds according to the invention, as well as their salts, are endowed with highly advantageous pharmacological properties, and differ from the other 2,3-dihydro-2-oxobenzofuran compounds which are already known. In effect, in vivo pharmacological trials have shown that the compounds of the present invention exert a potent antihypoxic effect in animals.

During aging or as a consequence of a stroke, increased cell fragility and vulnerability are important physiopathological components, stimulating the search for new therapeutic agents directed towards protecting the brain, which is placed in the position of being unable to respond to any further attack originating from its surroundings.

An attack of this kind may be repeated in the form of a deficiency in the oxygen supply, and for this reason, in respect of their consequences, there is a close analogy between hypoxia and cerebral aging. This analogy is expressed, in particular, by a fall in the energy reserves of the brain, a lower resistance to stress and a fall in the renewal of the oxygen-dependent synthesis of neurotransmitters.

The compounds of the present invention were tested in respect of their capacity to prolong the survival of cerebral tissue during acute hypoxia in mice, or to maintain the level of tissue energy-rich compounds in rats subjected to a fall in the oxygen supply [Pharmacology of Cerebral Ischemia, (1968) p. 334–339 Elsevier Science Publishers B.V., J. Krieglstein ed.]. In both types of experiment that were carried out, the compounds of the invention were compared with reference compounds, namely meclofenoxate, pyritinol and piracetam [Arz. Forsch. Drug Res. (1986), 36 II No. 9, p. 1314–1320].

The latter were chosen on account of their therapeutic indications with respect to symptoms associated with senescence or to the sequelae of stroke, the indications being claimed on the basis of the antihypoxic and nootropic effect without the production of a vascular effect. Compounds of the myolitic or adrenolytic type were hence excluded.

The pharmacological trials in mice demonstrated that the compounds of the present invention have an antihypoxic protective effect which is 2 to 4 times as potent as that of the most active reference compound. In rats subjected to hypoxia, the compounds of the invention exerted the same protective effects on cerebral energy as the reference compounds, but at doses which are at least 3-fold lower, and thus confirmed the great advantage of their use in therapy.

By significantly counteracting brain death and tissue energy lack in the case of insufficiently of the oxygen supply, the compounds of the present invention exert a pronounced antihypoxic effect and are hence useful in cases of acute, transitory or progressive ischemic syndromes localized in any part of the body, since they exert their pharmacological properties with respect to the lack of oxygenation which accompanies these accidents. Their pharmacological properties enable them to be applied in the correction of disorders linked to hypoxemia and to energy insufficiency, for example, during cerebral aging.

The invention also encompasses the pharmaceutical compositions containing as active principle at least one compound of general formula I or one of its salts with a pharmaceutically compatible inorganic or organic base or acid, in combination with one or more suitable inert excipients.

The pharmaceutical compositions thereby obtained are advantageously presented in various forms, such as, for example, tablets, dragees, gelatin capsules, sublingual tablets or other galenical preparations suitable for sublingual administration, suppositories, injectable solutions or solutions to be taken by mouth.

The dosage can vary widely depending on the patient's age and weight, the nature and severity of the condition and also the administration route.

The preferred administration route is the oral or parenteral route. Generally speaking, the unit dose will range between 0.5 and 300 mg, and the daily dosage usable in human therapy between 0.5 and 900 mg.

The examples which follow, given without implied limitation, illustrate the invention.

The melting points stated are measured according to the micro-Köfler technique. The infrared spectra are obtained with solutions of the products in Nujol. The proton nuclear magnetic resonance (NMR) spectra were recorded at 60 MHz.

EXAMPLE 1

2-(2,3-Dihydro-2-oxo-3-phenyl-5-benzofuranyl)acetamide 190 ml of 80% strength sulfuric acid solution are added to a mixture of 16 g of mandelic acid and 15 g of 4-hydroxyphenylacetamide [J. Am. Chem. Soc. (1946) p. 2633]. The medium is heated very rapidly to 80° C. and immediately hydrolyzed using 600 g of ice. The aqueous phase is extracted with 3 times 200 ml of chloroform and the organic phase washed with saturated sodium bicarbonate solution, dried over anhydrous sodium sulfate and concentrated under vacuum. The crude product obtained is recrystallized in chloroform.

Yield: 20%

Melting point: 162° C.

The spectral physical constants of this compound are shown in Table I.

EXAMPLE 2

N-Benzyl-2-(2,3-dihydro-2-oxo-3-phenyl-5-benzofuranyl)acetamide

STAGE A

N-Benzyl-4-hydroxyphenylacetamide

A mixture of 80 g of 4-hydroxyphenylacetic acid methyl ester and 51.6 g of benzylamine is brought to 180° C. for 8 hours. The mixture is allowed to return to room temperature and the crystals are filtered off and washed with ethanol and then ethyl ether.

Yield: 55%

Melting point: 149°–150° C.

STAGE B 200 ml of 85% strength sulfuric acid are added to a mixture of 53.4 g of amide obtained above and 26.2 g of mandelic acid. The medium is brought as rapidly as possible to 120° C. while being stirred. It is hydrolyzed using a mixture of ice and ethyl acetate (50:50 v/v). The organic phase is washed using saturated sodium bicarbonate solution and then with water, dried over anhydrous magnesium sulfate and concentrated under vacuum. 36 g of crude solid product are obtained, which is recrystallized in an ethanol/water mixture.

Yield: 15%

Melting point: 164° C.

The spectral physical constants of this compound are shown in Table I.

EXAMPLE 3

2-(2,3-Dihydro-2-oxo-3-phenyl-5-benzofuranyl)-1-[4-(5-trifluoromethyl-2-pyridyl)piperazinyl]-1-oxoethane

STAGE A 2-(2,3-Dihydro-2-oxo-3-phenyl-5-benzofuranyl)acetic acid 75 g of mandelic acid and 75 g of 4-hydroxyphenylacetic acid are mixed in a round-bottomed flask. 800 ml of 80% strength sulfuric acid are added and the medium is then brought rapidly to 90° C. while being stirred. It is hydrolyzed with 2 kg of ice, the aqueous phase is extracted with 3 times 500 ml of ethyl acetate and the organic phase is washed with water, dried over anhydrous sodium sulfate and concentrated under vacuum. 117 g of a yellow oil are thereby obtained, which is purified by chromatography on 1200 g of silica (70–230 mesh), using a mixture of dichloromethane and methanol (98.5:1.5 v/v) as eluant. After evaporation of the solvent, the pure product is obtained.

Yield: 50%

Melting point: 136° C.

Proton NMR spectrum of the product dissolved in DMSO-$d_6$: 12.5 to 13 ppm, m, exchangeable 1H; 7.1 to 7.7 ppm, m, 8H; 5.4 ppm, s, 1H; 3.6 ppm, s, 2H.

STAGE B 2-(2,3-Dihydro-2-oxo-3-phenyl-5-benzofuranyl)acetyl chloride 36.3 ml of double-distilled thionyl chloride are added dropwise to a solution, stirred and heated to 70° C., of 67 g of the acid obtained above in 600 ml of anhydrous benzene. The medium is then heated to reflux for 2 hours, the solvent evaporated off under vacuum and the residual oil taken up 3 times with 150 ml of anhydrous benzene, which is then evaporated off under vacuum. The crystallized product is washed in petroleum ether and filtered off.

Yield: 95%

STAGE C

A solution of 7.4 g of acetyl halide obtained in the preceding stage in 300 ml of anhydrous benzene is stirred at 5° C., and a mixture of 7.85 g of triethylamine and 4.1 g of 4-(5-trifluoromethyl-2-pyridyl)piperazine dihydrochloride is added dropwise. The reaction mixture is stirred at room temperature for 45 minutes and washed twice with 100 ml of water, the organic phase is dried over anhydrous sodium sulfate, the solvent is evaporated off under vacuum and the 10.5 g of residual oil obtained are purified by chromatography on silica (230–400 mesh), using a mixture of dichloromethane and methanol (99:1 v/v) as eluant. After evaporation of the solvent, pure crystals are obtained.

Yield: 35%

Melting point: 55° C.

The spectral physical constants of 2-(2,3-dihydro-2-oxo-3-phenyl-5-benzofuranyl)-1-[4-(5-trifluoromethyl-2-pyridyl)piperazinyl]1-oxoethane are shown in Table I.

EXAMPLE 4

2-(2,3-Dihydro-2-oxo-3-phenyl-5-benzofuranyl)-1-[4-(3,4-methylenedioxybenzyl)piperazinyl]-1-oxomethane This compound was prepared according to the process described in Example 3, using 4-(3,4-methylenedioxybenzyl)piperazine in Stage C.

Yield: 48%

Melting point: approximately 70° C. (foam).

The spectral physical constants of this compound are shown in Table I.

EXAMPLE 5

2-(2,3-Dihydro-2-oxo-3-phenyl-5-benzofuranyl)-1-(4-methylpiperazinyl)-1-oxoethane tartrate 2-(2,3-Dihydro-2-oxo-3-phenyl-5-benzofuranyl)-1-(4-methylpiperazinyl-1-oxoethane was prepared according to the process described in Example 3, but using 4-methylpiperazine in Stage C. The latter compound was dissolved in a solution of DL-tartaric acid to form the corresponding salt, and then recrystallized in ethyl ether.

Yield: 38%

Melting point of the salt: 108° C.

The spectral physical constants of this salt are shown in Table I.

TABLE I

COMPOUNDS OF FORMULA

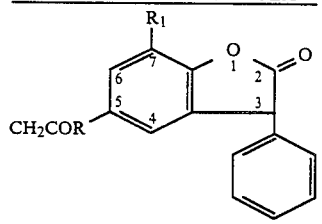

| Ex | $R_1$ | R | IR(cm$^{-1}$) $\nu$C=O lactone | IR(cm$^{-1}$) $\nu$C=O extracyclic | NMR (solvent) |
|---|---|---|---|---|---|
| 1 | —H | —NH$_2$ | 1800 | 1655 | (CDCl$_3$ + DMSO—d$_6$) 7.1 7.6 ppm,m,8H; 6.2 to 6.8 ppm,m, exchangeable 2H 5.5 ppm,s,1H; 3.4 ppm,s,2H |
| 2 | —H | —NHCH$_3$—C$_6$H$_5$ | 1810 | 1640 | (CDCl$_3$ + DMSO—d$_6$) 7 to 7.4 ppm,m,13H + exchangeable 1H 4.8 ppm,s,1H; 4.3 ppm,d,2H; 3.4 ppm,s,2H |
| 3 | —H | piperazinyl-pyridinyl-CF$_3$ | 1810 | 1645 | (CDCl$_3$) 8.4 to 8.7 ppm,m,1H; 7.6 ppm,d,1H; 7 to 7.5 ppm,m,8H; 6.6 ppm,d,1H; 4.9 ppm,s,1H; 3.7 ppm,s,2H; 3.4 to 3.6 ppm,m,8H |
| 4 | —H | piperazinyl-N-CH$_3$-methylenedioxyphenyl | 1810 | 1640 | (CDCl$_3$) 6.8 to 7.8 ppm,m,11H; 6.05 ppm,s,2H; 5 ppm,s,1H; 3.7 ppm,s,2H; 3.3 to 3.6 ppm,m,4H; 3.4 ppm,s,2H; 2.1 to 2.5 ppm,m,4H |
| 5 | —H | piperazinyl-N—CH$_3$ | 1805 | 1725 (acid) 1650 (amide) | (D$_2$O) 7 to 8 ppm,m,8H; 5.5 ppm,s,1H; 4.7 ppm,s,2H; 4.6 ppm,s,2H; 2.8 to 4.6 ppm,m,11H |

EXAMPLE 6

2-(2,3-Dihydro-2-oxo-3-phenyl-7-benzofuranyl)-1-morpholino-1-oxoethane

STAGE A 2-(2-Hydroxyphenyl)-1-morpholino-1-oxoethane 27.3 g of morpholine are added in a single portion to a solution of 30 g of 2,3-dihydro-2-benzofuranone in 100 ml of ethanol, and the medium is stirred for 1 hour. The solvent is evaporated off under vacuum, the residual gum is taken up in isopropyl ether in the hot state and the medium is allowed to return to room temperature. The crystallized product is filtered, washed with isopropyl ether and dried. 45 g of white crystallized product are obtained.

Melting point: 122° C.

STAGE B 30.5 g of a product obtained in the preceding stage and 23 g of mandelic acid are mixed in an Erlenmeyer. 150 ml of 85% strength sulfuric acid are added at room temperature and the medium is boiled as rapidly as possible to 120° C. while being stirred. The reaction mixture is immediately immersed in 1 liter of a mixture of ethyl acetate and ice (50:50 v/v). Settling is allowed to occur, the organic phases are combined and washed with saturated sodium bicarbonate solution, the organic phase is dried over anhydrous sodium sulfate, the solvent is evaporated off under vacuum and the crude product is recrystallized in a mixture of ethanol and water (60:40 v/v) to collect white crystals.

Yield: 22%

Melting point: 147° C.

The spectral physical constants of this compound are shown in Table II.

EXAMPLES 7 AND 8

These compounds were prepared according to the process described in Example 6, but condensing 2-benzofuranone in Stage A with the appropriate amines. The spectral physical constants of these amides are shown in Table II.

EXAMPLE 7

N,N-Dimethyl-2-(2,3-dihydro-2-oxo-3-phenyl-7-benzofuranyl)-acetamide

Yield: 18%
Melting point: 134° C.

EXAMPLE 8

2-(2,3-Dihydro-2-oxo-3-phenyl-7-benzofuranyl)acetamide

Yield: 30%
Melting point: 218° C.

EXAMPLE 9

2-(5-Chloro-2,3-dihydro-2-oxo-3-phenyl-7-benzofuranyl)acetamide

This compound was prepared according to the process described in Example 6, but using 5-chloro-2,3-dihydro-2-benzofuranone and ammonia solution in Stage A.

Yield: 45%
Melting point: 162° C.

These spectral physical constants are shown in Table II.

TABLE II

COMPOUNDS OF FORMULA

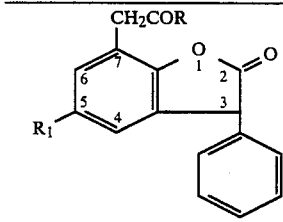

| Ex | $R_1$ | R | IR(cm$^{-1}$) $\nu$C=O lactone | IR(cm$^{-1}$) $\nu$C=O extracyclic | NMR (solvent) |
|---|---|---|---|---|---|
| 6 | —H | —N(morpholine) | 1805 | 1650 | (CDCl$_3$) 7.1 to 7.5 ppm,m,8H; 4.9 ppm,s,1H; 3.75 ppm,s,2H; 3.65 ppm,s,8H |
| 7 | —H | —N(CH$_3$)$_2$ | 1810 | 1640 | (CDCl$_3$) 7 to 7.4 ppm,m,8H; 4.9 ppm,s,1H; 3.75 ppm,s,2H; 3.05 ppm,s,3H; 2.95 ppm,s,3H |
| 8 | —H | —NH$_2$ | 1800 | 1650 | (CDCl$_3$ + DMSO—d$_6$) 7 to 7.5 ppm,m,8H; 6 to 6.9 ppm,m, exchangeable 2H, 5.3 ppm,s,1H; 3.6 ppm,s,2H |
| 9 | —Cl | —NH$_2$ | 1810 | 1655 | (CDCl$_3$ + DMSO—d$_6$) 7.1 to 7.6 ppm,m,7H; 5.5 a 6.5 ppm,m, exchangeable 2H, 5 ppm,s,1H; 3.55 ppm,s,2H |

PHARMACOLOGICAL STUDY

EXAMPLE 10

Acute hypoxia in mice

Male CD1 mice (Charles River) which have received intraperitoneally the test compound or a reference compound 30 minutes beforehand are subjected to an acute hypoxia of the hypobaric type. For this purpose, they are placed in an enclosure in which the atmospheric pressure can be rapidly lowered (in the space of 30 seconds) to a value of 160 mbar, which causes the death of all the animals approximately 15 seconds after this hypoxic pressure has been attained.

The survival of the brain is assessed by measuring the time at which the final respiratory gasp is observed.

The survival time of a treated batch is compared with that of a control batch receiving only the solvent.

The percentage increase in the survival time after the animals are treated with the compounds of the invention is shown in Table III. The significant results are underlined (p<0.05).

As seen in Table III, the compounds of the invention exert a potent antihypoxic effect, which is greatly superior to that of the reference compounds. In effect, at a dose of 100 mg/kg, meclofenoxate, pyritinol and piracetam increased the brain survival time of the animals by only 22%, 27% and 11%, respectively. The protection is significant only in the case of pyritinol.

At the same dose, the compounds of the invention have a much more potent protective effect than the latter compound. The increase in the survival time is, for example, 170% for the compound of Example 1, 133% for the compound of Example 4 and 111% for the compound of Example 5.

TABLE

| | Percentage increase in the survival time | | | |
|---|---|---|---|---|
| | DOSES mg/kg(I.P.) | | | |
| COMPOUND | 3 | 10 | 30 | 100 |
| Meclofenoxate | | | +4 | +22 |
| Pyritinol | | | +13 | +27 |
| Piracetam | | | | +11 |
| Ex. 1 | +24 | | +46 | +170 |
| Ex. 3 | | | +36 | +57 |
| Ex. 4 | +43 | +49 | +54 | +133 |
| Ex. 5 | | | | +111 |
| Ex. 8 | | | | +13 |
| Ex. 9 | | | | +23 |

EXAMPLE 11

Acute hypoxia in rats

Male Fischer 344 rats (Charles River) which have received the test compound or a reference compound 30 minutes beforehand are subjected to a deficiency in the oxygen supply by being placed in a normobaric enclosure in which the composition of the circulating gaseous mixture may be changed accurately. Whereas the control rats breathe a gaseous mixture containing 21% of oxygen and 79% of nitrogen, the rats subjected to hypoxia breath a mixture of 3% oxygen and 97% nitrogen for 2 minutes.

At the end of the hypoxic period, the animals are rapidly sacrificed by total immersion in liquid nitrogen. The frozen brain is removed and the energy-rich compounds (ATP, ADP, AMP) are extracted and assayed by the luciferin luminescence method.

The tissue energy content (EC) is calculated according to ATKINSON's formula:

$$EC = \frac{ATP + \frac{1}{2}ADP}{ATP + ADP + AMP}$$

The results of this study are shown in Table IV.

In the control animals, hypoxia leads to a slump in the tissue ATP level ($-74.2\%$) which is accompanied by a rise in the mono- and diphosphate compounds (AMP, ADP). This is reflected in the fall in the total energy content ($-25.3\%$).

At a dose of 300 mg/kg, piracetam exerts only very little protection, inhibiting by only 3.9% the effects of hypoxia on the ATP level.

At the same dose, meclofenoxate inhibits by 59.7% and 69.6%, respectively, the effects of hypoxia on the ATP level and the energy content. Such an effect is observed with a dose of 30 mg/kg of the compound of Example 1.

Under the same conditions, pyritinol at a dose of 100 mg/kg exerts only a more modest effect. The fall in ATP is inhibited by 23% while that in the energy content is inhibited by 35%.

TABLE IV

| ACUTE HYPOXIA IN RATS | | | |
|---|---|---|---|
| Control rats in normoxia ATP = 2.373 μmoles/g | | EC = 0.959 | |
| Control rats in hypoxia ATP = 74.2% | | EC = 25.3% | |
| COMPOUND | DOSE mg/kg I.P. | % INHIBITION OF THE EFFECTS OF HYPOXIA | |
| | | ATP | EC |
| Meclofenoxate | 300 | 59.7 | 69.6 |
| Pyritinol | 030 | 11.1 | 16.6 |
| | 100 | 23.3 | 35.2 |
| Piracetam | 300 | 3.9 | 1.6 |
| Example 1 | 030 | 64.6 | 66 |

PHARMACEUTICAL PREPARATION

EXAMPLE 12

Gelatin capsules containing a 20-mg dose of 2-(2,3-dihydro-2-oxo-3-phenyl-5-benzofuranyl)acetamide

| | |
|---|---|
| 2-(2,3-Dihydro-2-oxo-3-phenyl-5-benzofuranyl)- acetamide | 20 mg |
| Corn starch | 15 mg |
| Lactose | 25 mg |
| Talc | 5 mg |

For a No. 3 gelatin capsule.

We claim:

1. A compound of the general formula I

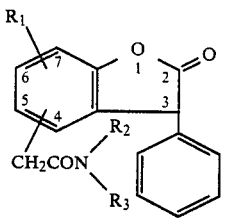

(I)

in which:

either $R_1$ is at the 7-position and the acetamido group is at the 5-position, or $R_1$ is at the 5-position and the acetamido group is at the 7-position, $R_1$ is a hydrogen or halogen atom, $R_2$ $R_3$, which may be identical or different, each is a hydrogen atom or a linear or branched alkyl radical containing 1 to 4 carbon atoms, or a benzyl radical optionally substituted or with a halogen atom, with an alkoxy radical containing 1 to 4 carbon atoms, or with an alkyl radical having 1 to 4 carbon atoms, or with a 3,4-methylenedioxy radical, or an addition salt thereof with a pharmaceutically-acceptable inorganic or organic acid.

2. A compound of the formula I'

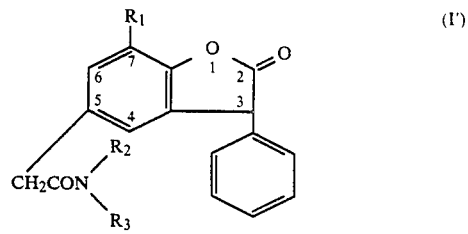

(I')

in which $R_1$ is a hydrogen or halogen atom, $R_2$ and $R_3$, which may be identical or different, each is a hydrogen atom or a linear or branched alkyl radical containing 1 to 4 carbon atoms, or a benzyl radical optionally substituted or with a halogen atom, with an alkoxy radical containing 1 to 4 carbon atoms, or with an alkyl radical having 1 to 4 carbon atoms, or with a 3,4-methylenedioxy radical, or an addition salt thereof with a pharmaceutically-acceptable inorganic or organic acid.

3. Compound of claim 1 being 2-(2,3-Dihydro-2-oxo-3-phenyl-5-benzofuranyl)acetamide or an addition salt thereof with a pharmaceutically acceptable inorganic or organic acid.

4. A method of treating a disease linked to hypoxemia and to energy insufficiency or cerebral aging in a subject suffering therefrom comprising the step of administering to the said subject an amount of a compound of claim 1 which is effective for the alleviation of such disease.

5. A pharmaceutical composition suitable for use in the treatment of a disease linked to hypoxemia and to energy insufficiency or cerebral aging comprising as active ingredient an amount of a compound of claim 1 which is effective for said purpose, in combination or as a mixture with a pharmaceutically-acceptable non-toxic inert vehicle or excipient.

6. Compound of claim 1 being N-benzyl-2-(2,3-dihydro-2-oxo-3-phenyl-5-benzofuranyl)acetamide or an addition salt thereof with a pharmaceutically-acceptable inorganic or organic acid.

7. Compound of claim 1 being N,N-dimethyl-2-(2,3-dihydro-2-oxo-3-phenyl-7-benzofuranyl)acetamide or an addition salt thereof with a pharmaceutically-acceptable inorganic or organic acid.

8. Compound of claim 1 being 2-(2,3-dihydro-2-oxo-3-phenyl-7-benzofuranyl)acetamide or an addition salt thereof with a pharmaceutically-acceptable inorganic or organic acid.

9. Compound of claim 1 being 2-(5-chloro-2,3-dihydro-2-oxo-3-phenyl-7-benzofuranyl)acetamide or an addition salt thereof with a pharmaceutically-acceptable inorganic or organic acid.

* * * * *

UNITED STATES PATENT AND TRADEMARK OFFICE
CERTIFICATE OF CORRECTION

PATENT NO. : 4,812,469
DATED : March 14, 1989
INVENTOR(S) : Gilbert Lavielle and Jean Lepagnol It is certified that error appears in the above-identified patent and that said Letters Patent is hereby corrected as shown below:

Col. 4, line 20; "insufficiently" should read -- insufficiency --
Col. 10, line 10; "TABLE" should read -- TABLE III --
Col. 11, line 57; delete "general"
Col. 12, line 5; "$R_2 R_3$," should read -- $R_2$ and $R_3$, --
Col. 12, line 8; delete "or"
Col. 12, line 9; after "atom," insert -- or --
Col. 12, line 31; delete "or"
Col. 12, line 32; after "atom," insert -- or --

Signed and Sealed this

Fifth Day of December, 1989

Attest:

JEFFREY M. SAMUELS

Attesting Officer    Acting Commissioner of Patents and Trademarks